(12) United States Patent
DiFiore (10) Patent No.: US 10,426,943 B2
(45) Date of Patent: Oct. 1, 2019

(54) INSERT FOR LUER CONNECTION

(75) Inventor: Attilio DiFiore, West Jordan, UT (US)

(73) Assignee: Attwill Medical Solutions Sterilflow L.P., Salt Lake City, UT (US)

(*) Notice: Subject to any disclaimer, the term of this patent is extended or adjusted under 35 U.S.C. 154(b) by 0 days.

(21) Appl. No.: 14/238,416

(22) PCT Filed: Aug. 10, 2012

(86) PCT No.: PCT/US2012/050348
§ 371 (c)(1),
(2), (4) Date: Jun. 24, 2014

(87) PCT Pub. No.: WO2013/023146
PCT Pub. Date: Feb. 14, 2013

(65) Prior Publication Data
US 2015/0306367 A1  Oct. 29, 2015

Related U.S. Application Data (60) Provisional application No. 61/522,592, filed on Aug. 11, 2011.

(51) Int. Cl.
*A61M 39/16* (2006.01)
*A61M 25/00* (2006.01)
(Continued)

(52) U.S. Cl.
CPC ........ *A61M 39/162* (2013.01); *A61M 5/3015* (2013.01); *A61M 25/00* (2013.01);
(Continued)

(58) Field of Classification Search
CPC .............. A61M 39/162; A61M 5/3015; A61M 25/0043; A61M 2025/0019;
(Continued)

(56) References Cited

U.S. PATENT DOCUMENTS 4,533,348 A   8/1985  Wolfe et al.
4,874,366 A  10/1989  Zdeb et al.
(Continued)

FOREIGN PATENT DOCUMENTS

CA   1173795 A    9/1984
EP   0353018 A1   1/1990
(Continued)

OTHER PUBLICATIONS

De Cock et al.; "Topical Heparin in the Treatment of Ligneous Conjunctivitis"; Ophthalmology; (Oct. 31, 1995); pp. 1654-1659; vol. 102, No. 11; <doi: pubmed: 9098258 >.
(Continued)

*Primary Examiner* — Kevin C Sirmons
*Assistant Examiner* — Leah J Swanson
(74) *Attorney, Agent, or Firm* — Thorpe North & Western, LLP (57) ABSTRACT

An insert for a luer-type catheter connection includes a fluid pathway connecting a female end and a male end. The male end is configured for slidable insertion into a female luer fitting of a catheter, and the female end is configured to receive a male luer nozzle of a fluid delivery device. The insert also includes a threaded collar having internal threading faced for coupling with the female luer fitting and external threading faced for coupling with a locking collar on the fluid delivery device. A cartridge located in the fluid pathway is configured to hold a patency agent and further to release the patency agent into the catheter when fluid is passed through the cartridge.

31 Claims, 6 Drawing Sheets

(51) Int. Cl.
*A61M 5/30* (2006.01)
*A61M 39/10* (2006.01)

(52) U.S. Cl.
CPC ..... *A61M 25/0043* (2013.01); *A61M 25/0097* (2013.01); *A61M 2025/0019* (2013.01); *A61M 2025/0056* (2013.01); *A61M 2039/1077* (2013.01); *A61M 2039/1094* (2013.01)

(58) Field of Classification Search
CPC ........ A61M 2025/0056; A61M 1/0096; A61M 2039/0036; A61M 2039/0285; A61M 2039/0205
USPC .................................................. 604/518, 533
See application file for complete search history.

(56) References Cited

U.S. PATENT DOCUMENTS

| | | | |
|---|---|---|---|
| 5,006,114 | A | 4/1991 | Rogers et al. |
| 5,024,657 | A * | 6/1991 | Needham ............ A61M 5/1409 604/251 |
| 5,030,203 | A | 7/1991 | Wolf, Jr. et al. |
| 5,049,139 | A | 9/1991 | Gilchrist |
| 5,098,394 | A | 3/1992 | Luther |
| 5,205,820 | A * | 4/1993 | Kriesel ............... A61M 5/1409 128/DIG. 12 |
| 5,395,323 | A | 3/1995 | Berglund |
| 5,547,471 | A | 8/1996 | Thompson et al. |
| 5,984,373 | A | 11/1999 | Fitoussi et al. |
| 6,105,442 | A | 8/2000 | Kriesel et al. |
| 6,406,879 | B2 | 6/2002 | James et al. |
| 6,702,850 | B1 | 3/2004 | Byun et al. |
| 6,805,685 | B2 | 10/2004 | Taylor |
| 7,045,585 | B2 | 5/2006 | Berry et al. |
| 7,081,109 | B2 | 7/2006 | Tighe et al. |
| 2003/0124705 | A1 | 7/2003 | Beny et al. |
| 2005/0124970 | A1 * | 6/2005 | Kunin ................. A61M 39/162 604/508 |
| 2007/0003603 | A1 * | 1/2007 | Karandikar ............ A01N 59/16 424/443 |
| 2007/0042015 | A1 | 2/2007 | Berry et al. |
| 2008/0027401 | A1 * | 1/2008 | Ou-Yang ........... A61M 25/0017 604/265 |
| 2008/0097407 | A1 * | 4/2008 | Plishka ............... A61M 39/045 604/533 |
| 2008/0140055 | A1 * | 6/2008 | Shirley ............... A61J 15/0015 604/535 |
| 2009/0163876 | A1 * | 6/2009 | Chebator ............ A61M 39/26 604/192 |
| 2009/0281059 | A1 | 11/2009 | Falotico et al. |
| 2010/0198148 | A1 | 8/2010 | Zinger et al. |
| 2011/0054440 | A1 | 3/2011 | Lewis |
| 2011/0066120 | A1 | 3/2011 | Lee |
| 2011/0257606 | A1 | 10/2011 | Truitt et al. |
| 2012/0083750 | A1 * | 4/2012 | Sansoucy ........... A61M 39/162 604/265 |
| 2013/0085474 | A1 | 4/2013 | Charles et al. |
| 2013/0172853 | A1 | 7/2013 | McClain et al. |
| 2013/0338644 | A1 | 12/2013 | Solomon et al. |

FOREIGN PATENT DOCUMENTS

| | | |
|---|---|---|
| EP | 1663299 A2 | 6/2006 |
| GB | 2187388 A | 9/1987 |
| JP | S60-138544 U1 | 9/1985 |
| WO | WO 86/03416 | 6/1986 |
| WO | WO 94/22522 | 10/1994 |
| WO | WO 2002/005873 | 1/2002 |
| WO | WO 2008/014440 | 1/2008 |
| WO | WO 2013/023146 | 2/2013 |
| WO | WO 2013/110956 A1 | 8/2013 |
| WO | WO 2015/109162 A1 | 7/2015 |

OTHER PUBLICATIONS

Fine et al.; "Successful Treatment of Ligneous Gingivitis with Warfarin"; Oral Surgery, Oral Medicine, Oral Pathology, Oral Radiology; (Jan. 1, 2009); pp. 77-80; vol. 107, No. 1; <doi:10.1016/j.tripleo.2008.08.007 >.

* cited by examiner

INSERT FOR LUER CONNECTION

BACKGROUND

Access devices, such as catheters, are subject to causing infection and can have biofouling issues. Infection and intervention rates on access catheters can vary based upon the type of catheter and duration of placement. Infection of long-term blood access devices in particular can be associated with blood stream infections that can lead to patient death. Interventions designed to rescue an access from removal due to clotting or biofouling often requires that the patient undergo a revision treatment where the access device is removed and replaced. In some cases, it is necessary to sacrifice the compromised access location and place the device in a secondary location in the patient. Extending the patency of access devices can improve the viability of long-term placement and reduce the need for subjecting patients to the expense and trauma of unnecessary additional intervention procedures.

DETAILED DESCRIPTION

Reference will now be made to the examples illustrated, and specific language will be used herein to describe the same. Features and advantages of the technology will be apparent from the detailed description which follows, taken in conjunction with the accompanying drawings, which together illustrate, by way of example, features of the technology.

It is to be noted that, as used in this specification and the appended claims, the singular forms "a," "an," and "the" include plural referents unless the context clearly dictates otherwise.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the description herein.

The term "catheter" is used herein to refer generally to devices used to provide fluid access to internal body spaces of a subject. This includes transcutaneous access as well as access through ducts, tracts, or passages of the subject's body. These access devices include, without limitation, venous catheters, arterial catheters, feeding tubes, injection ports, perfusion ports, urinary catheters, ventricular shunt ports, and the like.

The term "patency agent" is used to refer to agent(s) that promote, improve, or extend the viability of catheters, particularly by acting in the lumen of the catheter to prevent, retard, or ameliorate processes that compromise access or threaten patient health. Such processes include, without limitation, pathogenic invasion and infection, blood clotting, plaque buildup, and fungal growth.

Sizes, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1.0 to 2.0 percent" should be interpreted to include not only the explicitly recited values of about 1.0 percent to about 2.0 percent, but also include individual values and sub-ranges within the indicated range. Thus, included in this numerical range are individual values such as 1.1, 1.3, and 1.5, and sub-ranges such as from 1.3 to 1.7, 1.0 to 1.5, and from 1.4 to 1.9, etc. This same principle applies to ranges reciting only one numerical value. Furthermore, such an interpretation should apply regardless of the breadth of the range or the characteristics being described.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

The present disclosure is directed to devices and methods of extending the patency of catheters and other access devices. Typical use of access devices includes periodically accessing the device, e.g. to withdraw samples of blood or other bodily fluids or to deliver medicine. Such access devices often employ luer-type connections (e.g. luer lock connections) for connecting with fluid delivery and collection devices such as syringes, bottles, and bags. In one aspect, the present technology is particularly contemplated for use with access devices having a luer-type connection.

The present devices and methods are designed to protect the inner lumen of an access device between access events, at least in part through the delivery of a patency agent into the lumen of the access device. In one embodiment, the device is an insert that can be connected to an access end of the access device. In another aspect, the insert can be used between accesses in a process of patency locking in which a locking fluid is delivered into the catheter and remains there until the next access event, at which time the locking fluid is evacuated from the catheter.

The insert includes a number of features in accordance with this function, which will be described below. The insert is configured for insertion into the access end of an access device so as to communicate with the lumen of the access device. More particularly, the insert is designed to be interposed in a connection between the access device and a locking fluid delivery device, such as a needleless syringe. The insert is further configured to hold a patency agent and to release this agent into the lumen of the catheter when the locking fluid is charged therein.

Figure 1:
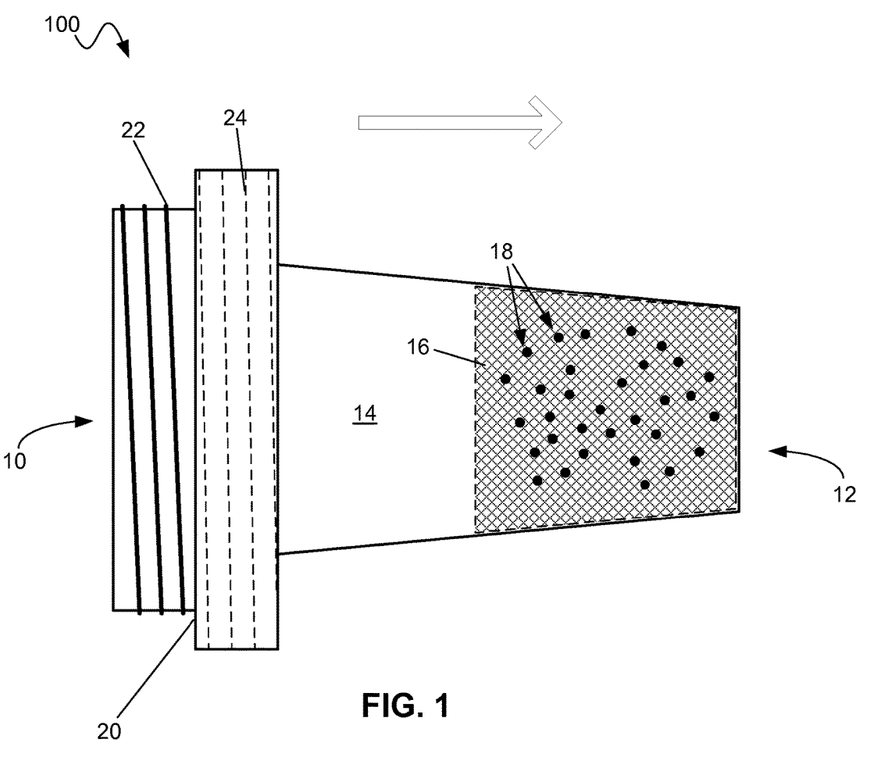
FIG. 1 is a schematic diagram of an example insert in accordance with the present technology.

The features and function of the insert may be described by reference to an example insert, such as the example shown in FIG. 1. It should be noted that FIG. 1 and subsequent FIGS. are schematics illustrating structural features of the devices described, and are not intended to convey scale. The insert 100 has a female end 10 and a male end 12 connected by a fluid pathway 14 extending through the insert. A cartridge 16 located in the fluid pathway is configured for admitting fluid flow, and also for holding a patency agent 18 before use and then releasing the agent when an appropriate fluid is flowed through the fluid pathway. For example, in a process of locking a catheter, a locking fluid can be delivered into the lumen of the catheter through the insert, where the direction of flow is indicated in FIG. 1 by an arrow. The patency agent in the cartridge is released into the locking fluid and enters the catheter with the fluid, thereby locking the patency agent in the lumen until the next access of the catheter, when the patency agent can be aspirated from the catheter.

To facilitate the imposition of the insert in a luer connection, the male end of the insert is configured for insertion into a female luer fitting at the access end of a catheter. The female end of the insert is configured to receive insertion of a male luer feature of a fluid delivery device, such as the nozzle of a syringe or tube. In an embodiment, the insert further includes features for participation in a luer-type connection. Referring again to the example in FIG. 1, a threaded collar 20 concentrically situated on the insert 100 can include threading of a size and pitch to interact with luer-type features on the connected devices. One such feature typically associated with male components of luer-type connection is a locking collar that engages with flanges or other protuberances on a female component. As shown, the threaded collar can include external threading 22 facing the female end 10 of the insert and situated to facilitate coupling of the insert with a fluid delivery device. Imposition of the insert in a luer-type connection is further facilitated by internal threading 24 facing the male end 12 of the insert and configured to engage a flange on the female luer fitting of the catheter or other access device.

Figure 2A:
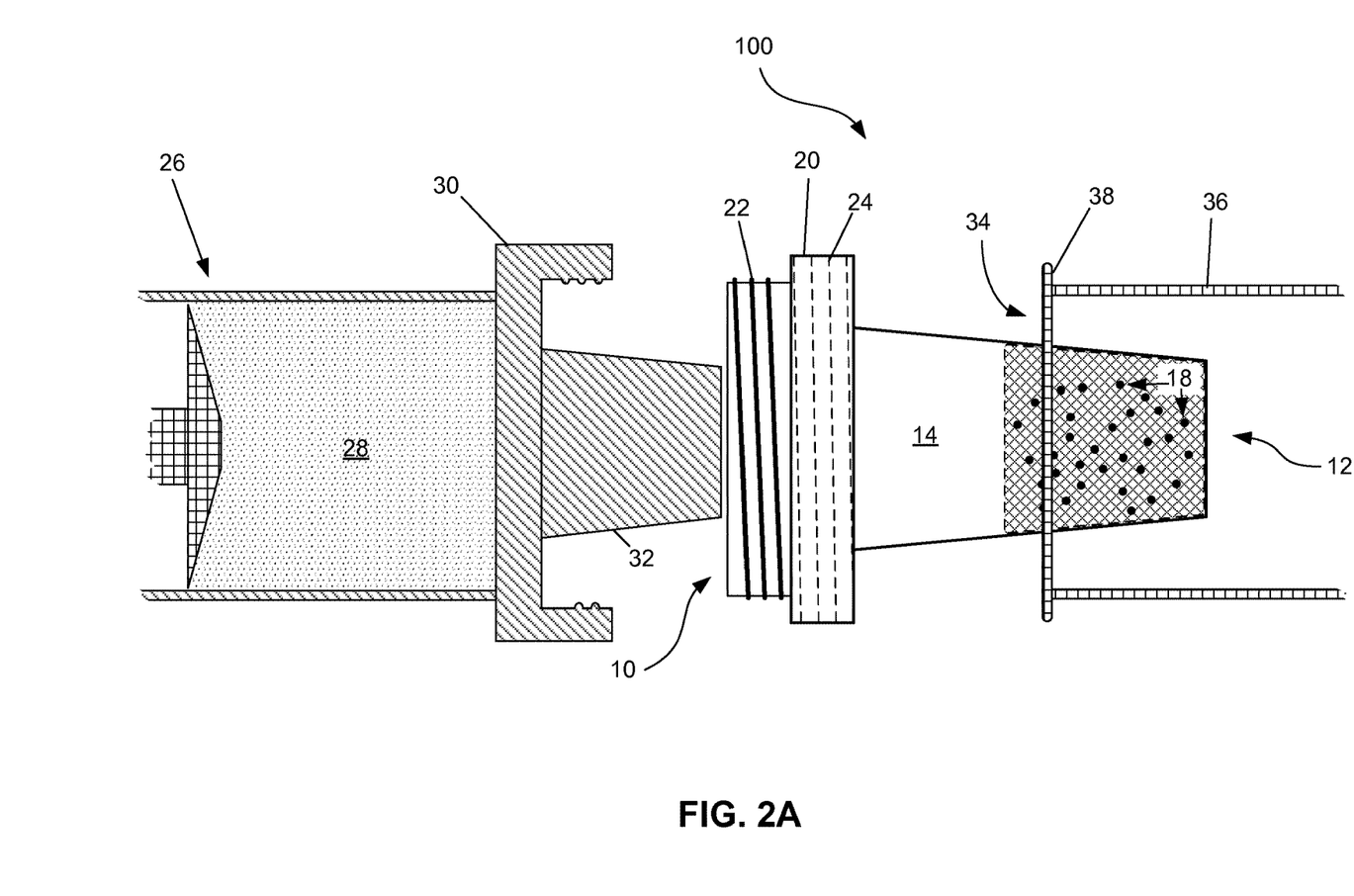
FIG. 2A is a schematic diagram of the example insert of FIG. 1 prior to coupling with a syringe and a catheter fitting.
Figure 2B:
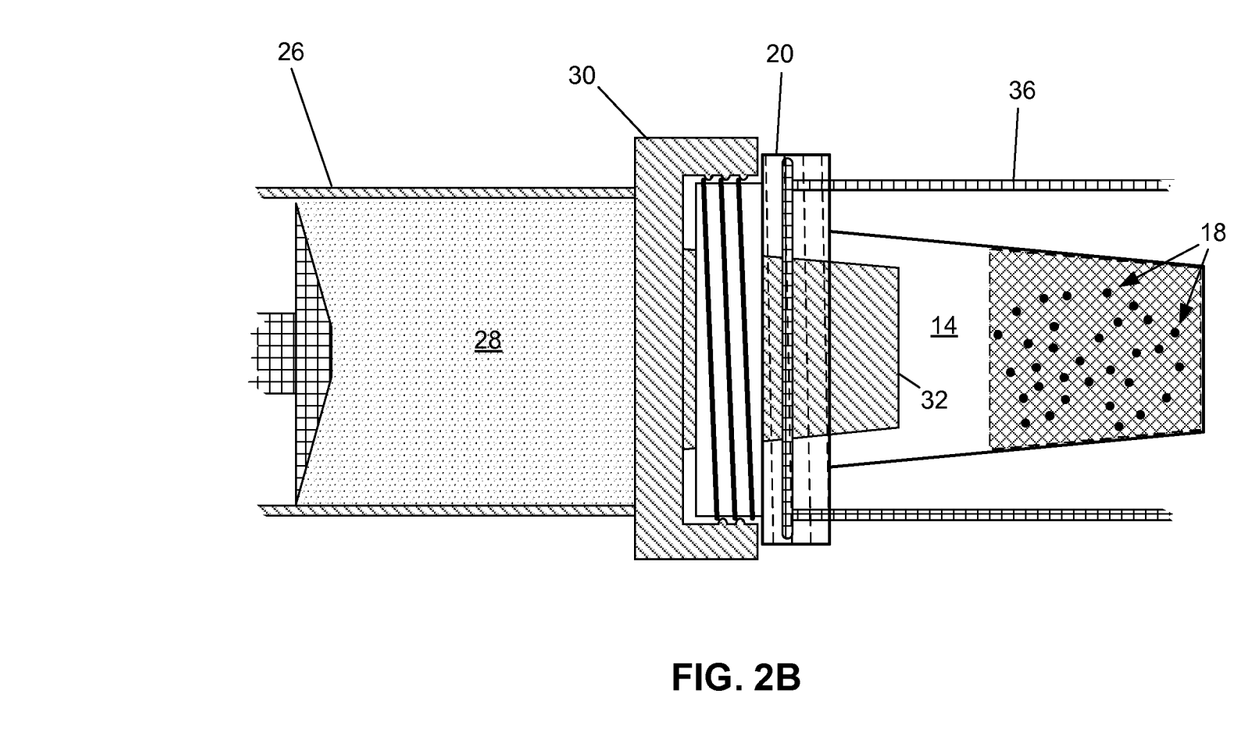
FIG. 2B is a schematic diagram of the example insert of FIG. 1 after coupling with a syringe and a catheter fitting.

The action of the collar in connecting the insert 100 is illustrated by the example shown in FIGS. 2A and 2B, in which the fluid delivery device is a syringe 26 filled with a locking fluid 28. When the syringe is inserted in the female end 10 of the insert, the spiral external threading 22 of the threaded collar 20 engages a locking collar 30 on the syringe. Screw coupling can be achieved by rotation of the syringe or insert until the syringe nozzle 32 is securely seated in the insert. A similar principle operates for the internal threading 24 facing the male end 12 of the insert. That is, when the male end of the insert is inserted into the female luer fitting 34 of a catheter 36, the flange 38 on the female luer fitting engages the internal threading so that relative rotation achieves coupling (a completed coupling is shown in FIG. 2B).

The fluid pathway inside the insert provides fluid communication with the lumen of the catheter and/or the lumen of a fluid delivery device. The dimensions of the fluid pathway from female end to male end can be selected to accommodate the luer fittings of the devices to be connected to the insert. In some cases, the dimensions of available fittings fall into one of a number of standard sizes. For example, International Organization for Standardization (ISO) specification 594 sets forth requirements for luer fittings for use with syringes and other medical transfusion apparatus. Under such standards, female fittings are larger than male fittings so as to provide an inner diameter that accommodates the outer diameter of the male fittings. One aspect of such fittings is a conical shape designed to provide a snug fit between components. As such, the lumens of such fittings typically exhibit a taper from a female end (if present) and/or toward a male end (if present). ISO-594 specifies a 6% taper. In an aspect, one or more of the dimensions of the insert are selected to conform to standard luer fittings. In one embodiment, the fluid pathway of the insert exhibits a taper extending from the female end toward the male end. In a specific embodiment the taper is about 6%.

Referring again to FIG. 1, the insert 100 includes a cartridge 16 that is situated in the fluid pathway 14 and configured to admit fluid flow through the fluid pathway. The cartridge can be made of any material that is suitable for admitting fluid flow and further for holding patency agent and then delivering the agent into the catheter lumen. Suitable materials include porous materials such as sponge-like materials, foam, a fiber matrix, or more a rigid porous material such as a ceramic. The cartridge can be shaped and sized to fit inside the insert and remain in place during use. Where the cartridge is made of a resilient material, the cartridge can be sized and shaped so as to be held in place by expansive pressure. The cartridge can be secured in place by other means such as adhesive, protuberances on the inner surface of the insert, or by a mesh screen, or any other feature that does not preclude sufficient fluid flow. The cartridge may also be a form of reservoir or collection of channels found within the connector which contains the patency agent in either liquid or solid form. Fluid introduced into the connector passes through the fluid pathway of the reservoir or channels, mixing with the patency agent.

Figure 3:
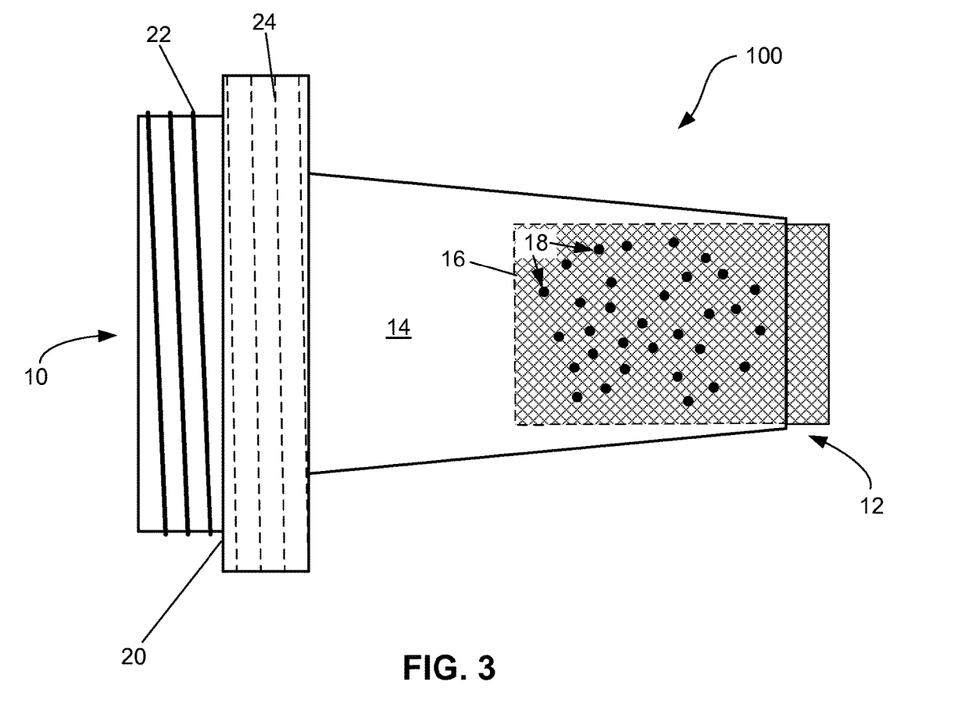
FIG. 3 is a schematic diagram of another example insert in accordance with the present technology.

The cartridge can be placed in any position relative to the ends of the insert. In a particular embodiment, the cartridge is placed in or adjacent to the male end. In one example, the cartridge is situated wholly within the insert as shown in FIG. 1. For some uses, effective patency locking may be realized by exposing a substantial portion of the cartridge to the lumen of the access device. Accordingly, in another example of an insert 100 shown in FIG. 3 the cartridge 16 can extend past the male end 12 of the insert so that a portion of the cartridge extends into the lumen of the catheter when installed. In one aspect, the male end of the insert serves to guide the cartridge into the female fitting of the access device and position the cartridge within the volume of locking fluid. In another aspect, a longer cartridge can be used so as to accommodate greater amounts of patency agent. The size and shape of the cartridge can further be selected so as to leave an intervening space between the cartridge and the male fitting of a fluid delivery device coupled to the insert. This example is otherwise similar to that shown in FIG. 1, and includes has a female end 10 and a male end 12 connected by a fluid pathway 14 extending through the insert. The cartridge is located in the fluid pathway is configured for admitting fluid flow, and also for holding a patency agent 18 before use and then releasing the agent when an appropriate fluid is flowed through the fluid pathway. Again, a threaded collar 20 is concentrically situated on the insert can include threading of a size and pitch to interact with luer-type features on the connected devices, and can include external threading 22 facing the female end of the insert and situated to facilitate coupling of the insert with a fluid delivery device. Also included is an internal threading 24 facing the male end 12 of the insert and configured to engage a flange on the female luer fitting of the catheter or other access device.

Figure 4:
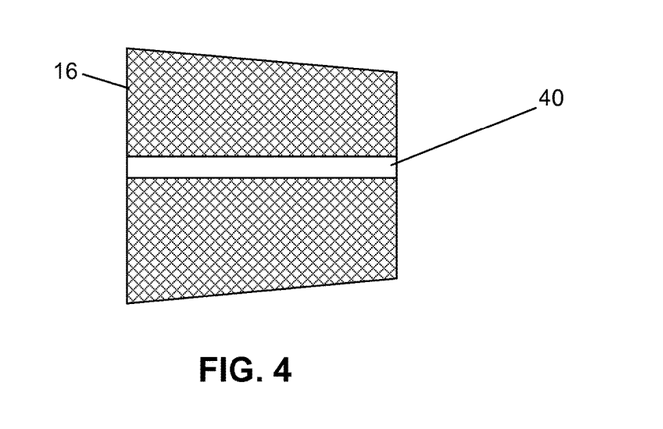
FIG. 4 is a cross-section diagram of an example cartridge in accordance with the present technology.

The cartridge material can be sufficiently porous to allow fluid flow that is adequate for charging the catheter. In a particular embodiment, an example of which is shown in FIG. 4, the cartridge can include an axial channel 40 extending axially therethrough. Such a channel 40 can serve to decrease resistance of a cartridge to the flow of fluid through the fluid pathway. In a specific embodiment, the axial channel may coincide with the center axis of the cartridge as illustrated in FIG. 4. In another aspect, the channel can serve as an interface for diffusion of patency agent into the fluid.

Figure 5A:
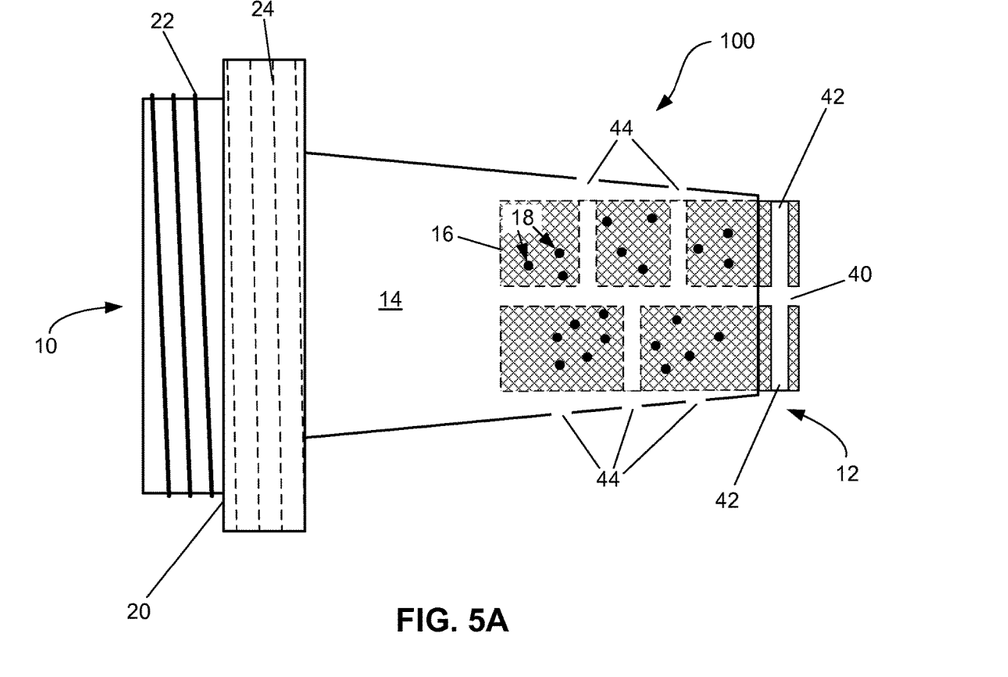
FIG. 5A is a schematic diagram of another example insert in accordance with the present technology.
Figure 5B:
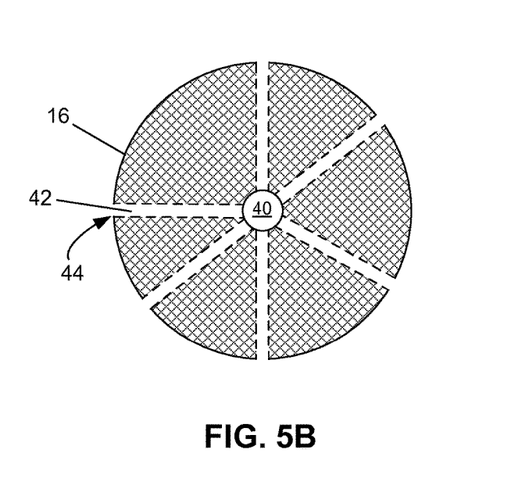
FIG. 5B cross-section diagram of a cartridge in accordance with the present technology.

In a further embodiment, the axial channel can communicate with the circumference of the cartridge via one or more radial channels 42 as shown in FIGS. 5A and 5B. As shown in FIG. 5A, the radial channels can be located at any point along the length of the axial channel, and can join the axial channel either singly or in groups. In a particular aspect, the radial channels extend perpendicularly with respect to the axial channel. In another aspect, as the cross-section of a cartridge shows in FIG. 5B the radial channels can radiate from the axial channel at a plurality of angles with respect to the central axis of the cartridge. By providing additional paths for fluid to flow through the cartridge, the radial channels can further decrease resistance and enhance the rate of flow through the insert. In another aspect, the radial channels can aid in distribution of the fluid. Where the cartridge extends past the male end 12, radial channels in the exposed portion of the cartridge can help to redistribute and backfill the infused fluid into the more proximal portions of the access device lumen.

Another feature for enhancing fluid flow can comprise one or more holes 44 penetrating the insert to provide fluid communication with the fluid pathway 14 and/or to expose portions of the cartridge to the lumen of the access device. In this aspect, holes can be included in conjunction with cartridges having channels as well as cartridges without channels. As shown in FIG. 5A, holes can be located adjacent a portion of the cartridge, providing an additional pathway for fluid within the cartridge to exit the insert. As also illustrated in FIG. 5A and also FIG. 5*b*, for inserts that include radial channels the holes can be positioned in correspondence with radial channels to complete communication between the axial channel and the lumen of an access device. In FIGS. 5*a* and 5*b*, other numerical references shown but not specifically discussed are similar to those described with respect to FIGS. 3 and 4.

In a particular embodiment the cartridge contains or can be loaded with a patency agent. The patency agent can include one or more active ingredients that promote patency of a catheter, or more specifically, that act against agents and processes that can compromise catheter patency or the health of the patient. Non-limiting examples of such active ingredients include antibiotics, antiseptics, antiviral agents, antithrombotic agents, and antifungal agents. The patency agent can also include other ingredients for promoting the function of the agent or the locking fluid, e.g. by providing appropriate tonicity, pH, and salinity.

The patency agent can be included in any form that can be held in the cartridge material while being releasable when locking the catheter. These can include liquid forms or solid forms such as powders, granules, crystals, and the like that are held in pore spaces within the cartridge. In one example, a suitable solid patency agent can be formulated to go into solution or suspension in the presence of a locking fluid. In another example, the cartridge is impregnated with a patency agent in fluid form which then dries and adheres to the cartridge material. Infusion of the cartridge with locking fluid then reconstitutes the patency agent for delivery into the catheter.

Figure 6:
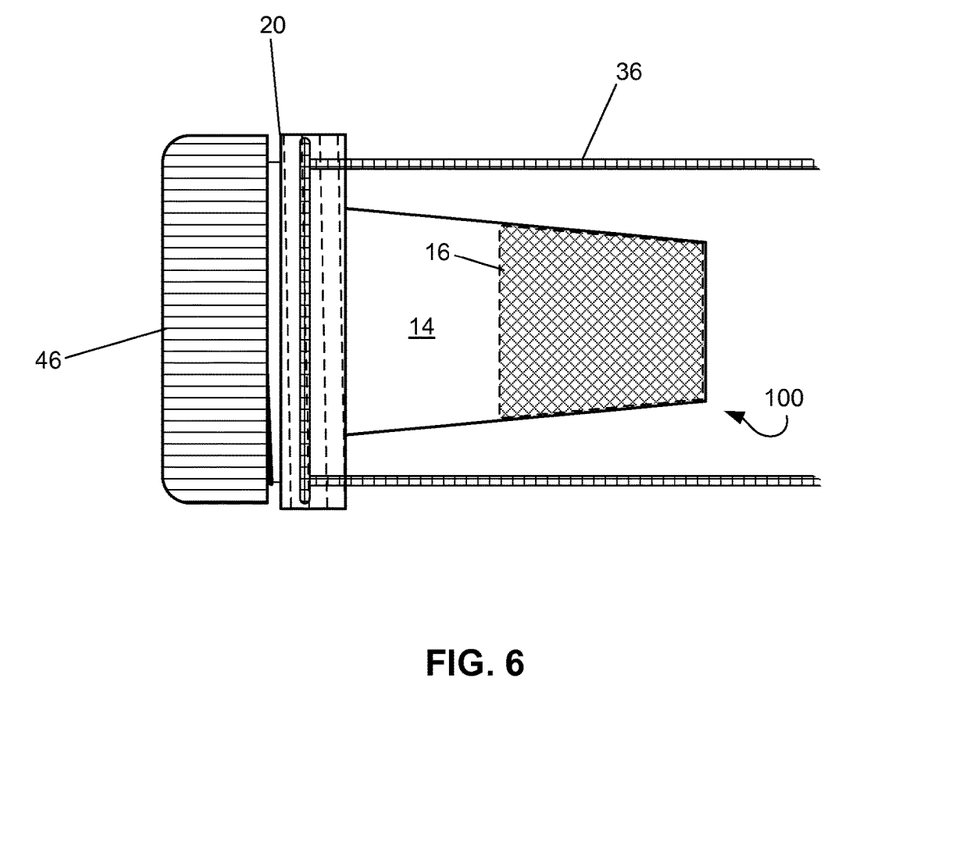
FIG. 6 is a schematic diagram of a capped insert coupled to a catheter in accordance with another example of the present technology.

The inserts of the present technology promote and extend patency in catheters by delivering patency agent into the lumen of the catheter. In this way a substantial length of the catheter can be exposed to the active ingredients. A further effect of this approach is that it can address biocontaminants that have already entered the catheter lumen during treatment. As a secondary function, the insert can also serve to cap the catheter between accesses, thereby preventing locking fluid from escaping from the catheter and also protecting the access port. For example, after charging of the catheter with locking fluid, the fluid delivery device can be uncoupled from the insert while leaving the insert coupled to the catheter. As shown in FIG. 6, the insert 100 can include an end cap 46 that can be removably attached to the female end of the insert. The end cap can serve as a barrier to seal the insert (and therefore the catheter 36) from access. Some access placements call for injectable end caps that can be penetrated by a needle and then self-seal. In a particular embodiment, the insert includes a self-sealing injectable end cap for this mode of use. Again, as shown is the cartridge 16, fluid pathway 14, and threaded collar 20.

Inserts described herein can be used in processes for locking catheters or other access devices that are fitted with luer-type connections. Such a process can include providing an insert as described above and in which the cartridge holds a patency agent, and coupling the male end of the insert to the female luer fitting of the catheter. A fluid delivery device is coupled to the female end of the insert, and then used to pass a locking fluid through the insert and into the lumen of the catheter. The patency agent is delivered into the lumen of the catheter along with the locking fluid, where both can remain until the next time the catheter is accessed. The locking procedure can further include leaving the insert coupled to the female luer fitting of the catheter. In a further aspect, the fluid delivery device can be replaced with an end cap at the female end of the insert.

In one aspect, the device is used to lock the catheter, and then removed for the following access. In a particular embodiment, the insert is employed on a single-use basis. The used device can be discarded and an unused device employed for a subsequent locking process.

While the forgoing examples are illustrative of the principles of the present technology in one or more particular applications, it will be apparent to those of ordinary skill in the art that numerous modifications in form, usage and details of implementation can be made without the exercise of inventive faculty, and without departing from the principles and concepts of this technology. Accordingly, it is not intended that the technology be limited, except as by the claims set forth below.

What is claimed is:

1. An insert for a luer-type catheter connection, comprising:
   a male end shaped for insertion into a female luer fitting of a catheter;
   a female end shaped to receive and attach to a male luer nozzle of a fluid delivery device;
   a fluid pathway connecting the female end and the male end;
   a cartridge located in the fluid pathway; and
   a patency agent held by the cartridge, wherein the patency agent comprises an antiseptic, wherein the cartridge is positioned for the patency agent to be released from the cartridge and into the catheter as a locking fluid flows through the fluid pathway and comes in direct contact with the patency agent to thereby lock the locking fluid and the patency agent within a lumen of the catheter, wherein the cartridge is sized and shaped such that locking fluid flows around the cartridge, and wherein the cartridge is sized and shaped to leave an intervening space between the cartridge and the male luer nozzle of the fluid delivery device when attached to the female end.

2. The insert of claim 1, further comprising a threaded collar having internal threading facing the male end for coupling with the female luer fitting of the catheter and external threading facing the female end for coupling with a locking collar on the fluid delivery device.

3. The insert of claim 1, wherein the patency agent is held by the cartridge in a particulate form.

4. The insert of claim 1, wherein the patency agent includes a liquid impregnating the cartridge.

5. The insert of claim 1, wherein the patency agent further includes an antimicrobial agent, an antiviral agent, an antifungal agent, an antithrombotic agent, or a combination thereof.

6. The insert of claim 1, wherein the cartridge comprises a porous material.

7. The insert of claim 6, wherein the porous material is a sponge material.

8. The insert of claim 6, wherein the porous material is a ceramic.

9. The insert of claim 1, wherein the cartridge includes an axial channel extending axially therethrough.

10. The insert of claim 9, wherein the cartridge further includes at least one radial channel in fluid communication with the axial channel.

11. The insert of claim 1, wherein the fluid pathway has an inward taper extending toward the male end.

12. The insert of claim 11, wherein the inward taper is about 6%.

13. The insert of claim 1, wherein the fluid delivery device is a needleless syringe.

14. The insert of claim 1, further including an end cap removably coupleable to the female end.

15. The insert of claim 14, wherein the end cap is a self-sealing injectable cap.

16. The insert of claim 1, further including at least one hole penetrating the insert along the fluid pathway.

17. The insert of claim 1, wherein the cartridge and the male end define an opening therebetween for the locking fluid to pass around the cartridge and into the lumen of the catheter with the patency agent released by the cartridge.

18. The insert of claim 1, wherein the cartridge located in the fluid pathway also extends beyond the male end.

19. The insert of claim 1, wherein the male end is shaped for slidable insertion into the female luer fitting of the catheter.

20. The insert of claim 1, wherein the cartridge is physically aligned directly between an opening of the fluid pathway at the male end where fluid exits the insert and a second opening of the fluid pathway at the female end where fluid enters the insert.

21. The insert of claim 1, wherein the insert is structured as an in-line fitting.

22. The insert of claim 1, wherein the patency agent further comprises an antithrombotic agent.

23. A method for locking a catheter, comprising:
connecting an insert to a catheter having a lumen and a female luer fitting, said insert comprising a male end, a female end, a fluid pathway connecting the female end and the male end, and a cartridge located in the fluid pathway and holding a patency agent therein, wherein the patency agent comprises an antiseptic, and wherein the connecting comprises inserting the male end into the luer fitting;
coupling a fluid delivery device containing locking fluid to the female end; and
flowing the locking fluid through the fluid pathway and into the catheter so that the locking fluid comes in direct contact with patency agent while flowing and the patency agent is delivered with the locking fluid into the lumen of the catheter, wherein the cartridge is sized and shaped such that locking fluid flows around the cartridge, and wherein the cartridge is sized and shaped to leave an intervening space between the cartridge and the fluid delivery device coupled to the female end.

24. The method of claim 23, wherein the insert further comprises a threaded collar having internal threading facing the male end for coupling with the female luer fitting of the catheter and external threading facing the female end for coupling with a locking collar on the fluid delivery device.

25. The method of claim 24, wherein the fluid delivery device is a needleless syringe.

26. The method of claim 25, wherein the patency agent further includes an antimicrobial agent, an antiviral agent, an antifungal agent, an antithrombotic agent, or a combination thereof.

27. The method of claim 26, wherein the patency agent is held by the cartridge in a particulate form.

28. The method of claim 27, wherein the patency agent includes a liquid impregnating the cartridge.

29. The method of claim 28, further comprising leaving the insert connected to the catheter until a subsequent access of the catheter.

30. The method of claim 29, further comprising uncoupling the fluid delivery device from the insert and attaching an end cap to the female end.

31. The method of claim 30, wherein the end cap is a self-sealing injectable cap.

* * * * *